US008325878B2

(12) United States Patent
McNutt et al.

(10) Patent No.: US 8,325,878 B2
(45) Date of Patent: Dec. 4, 2012

(54) REAL-TIME DOSE COMPUTATION FOR RADIATION THERAPY USING GRAPHICS PROCESSING UNIT ACCELERATION OF THE CONVOLUTION/SUPERPOSITION DOSE COMPUTATION METHOD

(75) Inventors: Todd McNutt, Severna Park, MD (US); Robert Allan Jacques, Burnaby (CA)

(73) Assignee: The Johns Hopkins University, Baltimore, MD (US)

( * ) Notice: Subject to any disclaimer, the term of this patent is extended or adjusted under 35 U.S.C. 154(b) by 141 days.

(21) Appl. No.: 12/934,513

(22) PCT Filed: May 8, 2009

(86) PCT No.: PCT/US2009/043341
§ 371 (c)(1),
(2), (4) Date: Sep. 24, 2010

(87) PCT Pub. No.: WO2009/137794
PCT Pub. Date: Nov. 12, 2009

(65) Prior Publication Data
US 2011/0051893 A1    Mar. 3, 2011

Related U.S. Application Data

(60) Provisional application No. 61/126,936, filed on May 8, 2008.

(51) Int. Cl.
*A61B 5/05* (2006.01)
(52) U.S. Cl. ....................................................... 378/65
(58) Field of Classification Search ................... 378/62, 378/64, 65; 600/407
See application file for complete search history.

(56) References Cited

U.S. PATENT DOCUMENTS

| | | | |
|---|---|---|---|
| 4,729,099 A | 3/1988 | Iverson et al. | |
| 5,596,653 A * | 1/1997 | Kurokawa | 382/128 |
| 5,602,892 A | 2/1997 | Llacer | |
| 6,148,272 A | 11/2000 | Bergstrom et al. | |
| 6,345,114 B1 | 2/2002 | Mackie et al. | |
| 6,560,311 B1 * | 5/2003 | Shepard et al. | 378/65 |
| 2002/0077545 A1 * | 6/2002 | Takahashi et al. | 600/424 |

OTHER PUBLICATIONS

International Search Report and Written Opinion for PCT/US2009/043341.

(Continued)

*Primary Examiner* — Irakli Kiknadze
(74) *Attorney, Agent, or Firm* — Venable LLP; Henry J. Daley

(57) ABSTRACT

A system for radiation therapy including a radiation planning system, wherein the radiation planning system comprises a parallel processor adapted to receive input information concerning a body having an intended radiation treatment region and to output information for providing radiation treatment to the intended radiation treatment region of the body, wherein the parallel processor is adapted to perform a plurality of reverse ray tracing calculations based on the input information concerning the body in determining the output information for providing radiation treatment, each of the plurality of reverse ray tracing calculations comprising: calculating a first physical property corresponding to a first sub-region of the intended radiation treatment region of the body that is intersected by a ray traced between a source position and the intended radiation treatment region; and calculating, subsequent to the first-mentioned calculating, a second physical property corresponding to a second sub-region of the intended radiation treatment region that is intersected by the ray at a location closer to the source position than is the first sub-region.

35 Claims, 12 Drawing Sheets

OTHER PUBLICATIONS

Otto, K., Med. Phys. 35, 2008, pp. 310-317, (published Dec. 26, 2007).
Yu, C.X., Phys. Med. Biol. 40, 1995, pp. 1435-1449.
Yan, D. et al., Phys. Med. Biol. 42, 1997, pp. 123-132.
Ahnesjo, A. et al., Phys. Med. Biol. 44, 1999, pp. R99-R155.
Mackie, T.R. et al., Med. Phys. 12, 1985, pp. 188-196.
Mackie, T.R. et al., Use of Comp. In Rad. Ther., 1987, pp. 107-110.
Papanikolaou, N. et al., Med. Phys. 20, 1993, pp. 1327-1336.
Ahnesjo, A., Acta. Oncol. 26, 1987, pp. 49-56.
Mackie, T.R. et al., Phys. Med. Biol. 33, 1988, pp. 1-20.
Amanatides, J. et al., Eurographics '87, Conference Proceedings, 1987.
Liu, H.H. et al., Med. Phys. 24, 1997, pp. 1729-1741.
Ahnesjo, A., Med. Phys. 16, 1989, pp. 577-592.
Lu, W., Phys. Med. Biol. 50, 2005, pp. 655-680.
Williams, L., Siggraph Comput. Graph. 17:3, 1983, pp. 1-11.
Mohan, R. et al., Med. Phys. 12, 1985, pp. 592-597.
McNutt, T.R., "Dose Calculations," Philips white paper.

\* cited by examiner

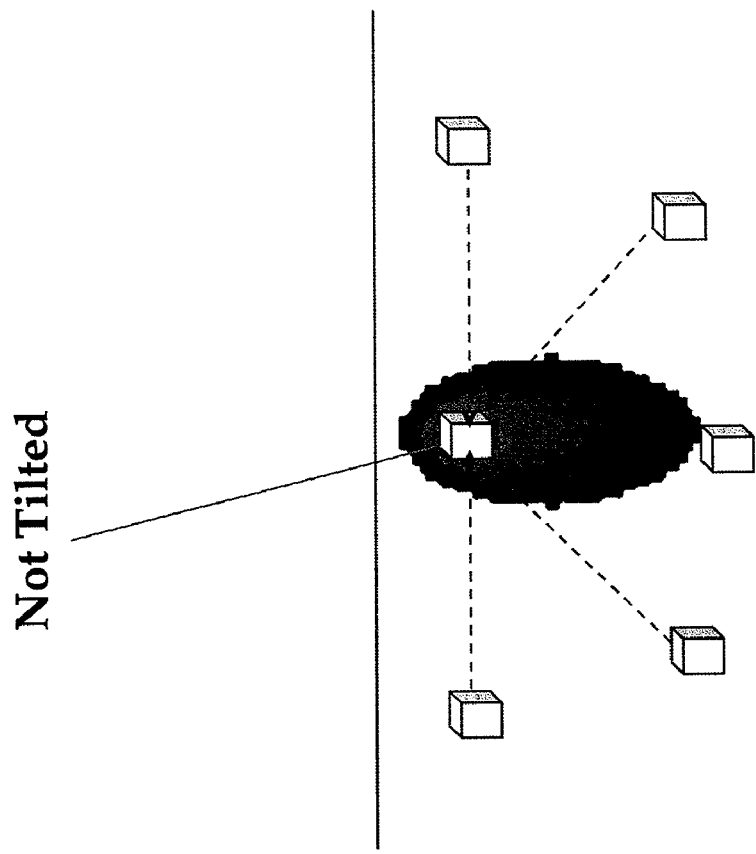
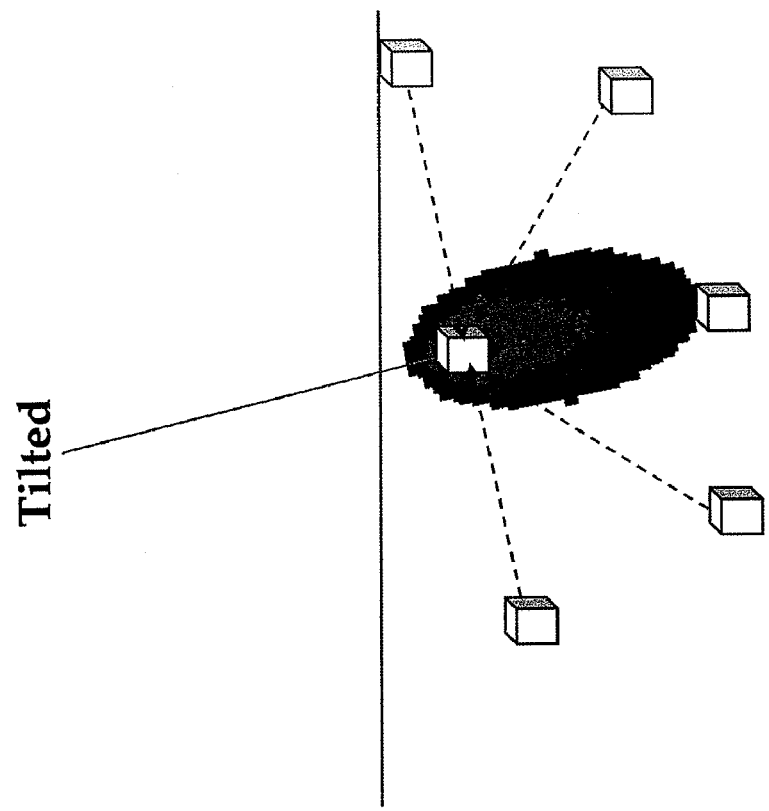

REAL-TIME DOSE COMPUTATION FOR RADIATION THERAPY USING GRAPHICS PROCESSING UNIT ACCELERATION OF THE CONVOLUTION/SUPERPOSITION DOSE COMPUTATION METHOD

CROSS-REFERENCE OF RELATED APPLICATION

This application claims priority to U.S. Provisional Application No. 61/126,936 filed May 8, 2008, the entire contents of which are hereby incorporated by reference, and is a U.S. national stage application under 35 U.S.C. §371 of PCT/US2009/043341 filed May 8, 2009, the entire contents of which are incorporated herein by reference.

BACKGROUND

1. Field of Invention

The current invention relates to radiation therapy systems, and more particularly external beam radiation therapy systems.

2. Discussion of Related Art

Radiation therapy is the medical use of radiation to treat malignant cells, such as cancer cells. This radiation can have an electromagnetic form, such as a high-energy photon, or a particulate form, such as an electron, proton, neutron, or alpha particle.

By far, the most common form of radiation used in practice today is high-energy photons. Photon absorption in human tissue is determined by the energy of the radiation, as well as the atomic structure of the tissue in question. The basic unit of energy used in radiation oncology is the electron volt (eV); $10^3$ eV=1 keV, $10^6$ eV=1 MeV. Three interactions can be involved in photon absorption in tissue: the photoelectric effect, Compton effect, and pair production.

In the photoelectric effect, an incoming photon transfers energy to a tightly bound electron. The photon transfers practically all of its energy to the electron and ceases to exist. The electron departs with most of the energy from the photon and begins to ionize surrounding molecules. This interaction depends on the energy of the incoming photon, as well as the atomic number of the tissue; the lower the energy and the higher the atomic number, the more likely that a photoelectric effect will take place. The energy range in which the photoelectric effect predominates in tissue is about 10-25 keV.

The Compton effect is the most important photon-tissue interaction for the treatment of cancer. In this case, a photon collides with a "free electron," i.e., one that is not tightly bound to the atom. Unlike the photoelectric effect, in the Compton interaction both the photon and electron are scattered. The photon can then continue to undergo additional interactions, albeit with a lower energy. The electron begins to ionize with the energy given to it by the photon. The probability of a Compton interaction is inversely proportional to the energy of the incoming photon and is independent of the atomic number of the material. The Compton effect dominates in the range of ~25 keV-25 MeV and is therefore the most common interaction occurring clinically, as most radiation treatments are performed at energies of about 6-20 MeV.

In pair production, a photon interacts with the nucleus of an atom. The photon gives up energy to the nucleus and, in the process, creates a positron-electron pair of particles. The positive electron (positron) ionizes until it combines with a free electron in positron-electron annihilation. This positron-electron annihilation generates two photons that travel in opposite directions. The probability of pair production is proportional to the logarithm of the energy of the incoming photon and is dependent on the atomic number of the material. The energy range in which pair production dominates is $\geqq 25$ MeV. This interaction occurs to some extent in routine radiation treatment with high-energy photon beams.

With the advent of high-energy linear accelerators, electrons have become a viable option in treating superficial tumors up to a depth of about 5 cm. Electron depth dose characteristics are unique in that they produce a high skin dose but exhibit a falloff after only a few centimeters.

Electron absorption in human tissue is greatly influenced by the presence of air cavities and bone. The most common clinical uses of electron beams include the treatment of skin lesions, such as basal cell carcinomas, and boosting of areas that have previously received photon irradiation, such as post-operative lumpectomy or mastectomy scar in breast cancer patients, as well as select nodal areas in the head and neck.

Fast, accurate dose computation algorithms are important for radiation therapy planning as they are the only available method of ensuring that the desired dose is delivered to a specific patient. Dose computation includes two parts: a source model and a transport model. The source model provides the incident fluence. The transport model computes the dose that results from the incident fluence and is currently the performance bottleneck. The three main transport algorithms in the order of increasing accuracy/decreasing performance are pencil beam, superposition/convolution, and Monte Carlo. Superposition/convolution is the current clinical standard method of calculating radiation dose for external beam radiation therapy.

In recent years, treatment quality has been increased by the use of intensity modulation. This technique uses a multi-leaf collimator to define multiple apertures from a single beam direction providing the ability to vary the intensity of radiation across the beam. This technique allows us to conform radiation treatment to the shape of the target and avoid critical structures while drastically increasing the number of beam parameters. In order to determine the best set of multi-leaf collimator settings, the treatment planning system must optimize, through multiple iterations of dose calculations, an objective function having the drastically increased number of beam parameters. In practice, the treatment planner repeats the optimizations multiple times in order to achieve the best results possible for the patient. Therefore, while a single optimization may take five minutes for a set of five beams, the entire process may take several hours to produce a clinically acceptable plan. This limits both the quantity and quality of intensity modulated plans in clinical work flow.

This clinical workflow limitation extends to more complex techniques such as volumetric modulated arc therapy (Otto, K., Med. Phys. 35, 310-317, 2008), intensity modulated arc therapy (Yu, C. X., Phys. Med. Biol. 40, 1435-1449, 1995), and adaptive radiation therapy (Yan, D., Vicini, F., Wong, J., Martinez, A, Phys. Med. Biol. 42, 123-132, 1997). Furthermore, this clinical workflow limitation prohibits real-time radiation therapy; the ability to scan, re-plan and treat every patient daily. A thorough review of dose calculation in radiation therapy is available from Ahnesjo et al. (Ahnesjo, A., Aspradakis, M, Phys. Med. Biol. 44, R99-R155 1999).

Thus, computational performance of the dose computation is a limiting factor in radiation therapy treatment plan quality. Traditionally, improvements in treatment quality have been realized by faster hardware. But, Moore's law has changed. Instead of doubling in speed every 18 months, computers are doubling the number of processing cores. And as processors are becoming multi-core, the many-core architectures of graphics processing units (GPUs) are gaining the flexibility to run general purpose algorithms. To realize the promised performance gains from the recent trend in computer hardware, traditional serial algorithms used in radiation dose computation should be replaced with parallel ones. Recently, Nucletron corporation made an announcement regarding GPU acceleration in their treatment planning system, though published details are not yet available. However, straight-forward partitioning of the existing serial algorithms to produce multiple threads for multiple processing cores does not work. This is because the threads are farmed out to calculate the same radiation dose based on the same input data and read/write conflicts may easily arise. When a write-on-write (WOW) conflict arises, for example, it can happen that only the last write is stored, leading to inaccurate dose calculations. Thus, there is a need in the art for improved dose calculation by utilizing parallel computing on multiple processing cores. There also remains a need for real-time dose calculation.

SUMMARY

Some embodiments of the current invention provides a system for radiation therapy comprising a radiation planning system, wherein the radiation planning system comprises a parallel processor adapted to receive input information concerning a body having an intended radiation treatment region and to output information for providing radiation treatment to the intended radiation treatment region of the body, wherein the parallel processor is adapted to perform a plurality of reverse ray tracing calculations based on the input information concerning the body in determining the output information for providing radiation treatment, each of the plurality of reverse ray tracing calculations comprising: calculating a first physical property corresponding to a first sub-region of the intended radiation treatment region of the body that is intersected by a ray traced between a source position and the intended radiation treatment region; and calculating, subsequent to the first-mentioned calculating, a second physical property corresponding to a second sub-region of the intended radiation treatment region that is intersected by the ray at a location closer to the source position than is the first sub-region.

Some embodiments of the current invention provide a method of determining radiation therapy parameters, comprising: obtaining information concerning an intended radiation treatment region of a body; computing, based on the information, in a direction from the body to a source position, a physical property at a first sub-region and a second sub-region along a ray that is traced between the source position and the body and intersecting the body in the intended radiation treatment region, the second sub-region along the ray being closer to the source position than the first sub-region along the ray; and determining the radiation therapy parameters for providing radiation treatment to the intended radiation treatment region based on the computing.

Some embodiments of the current invention provide a computer readable medium, when executed by a computer, causes the computer to implement the method above.

BRIEF DESCRIPTION OF THE DRAWINGS

Further objectives and advantages will become apparent from a consideration of the description, drawings, and examples.

FIGS. 7A and 7B illustrate titled kernel and non-tilted kernel during the superposition operation.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated.

Figure 1:
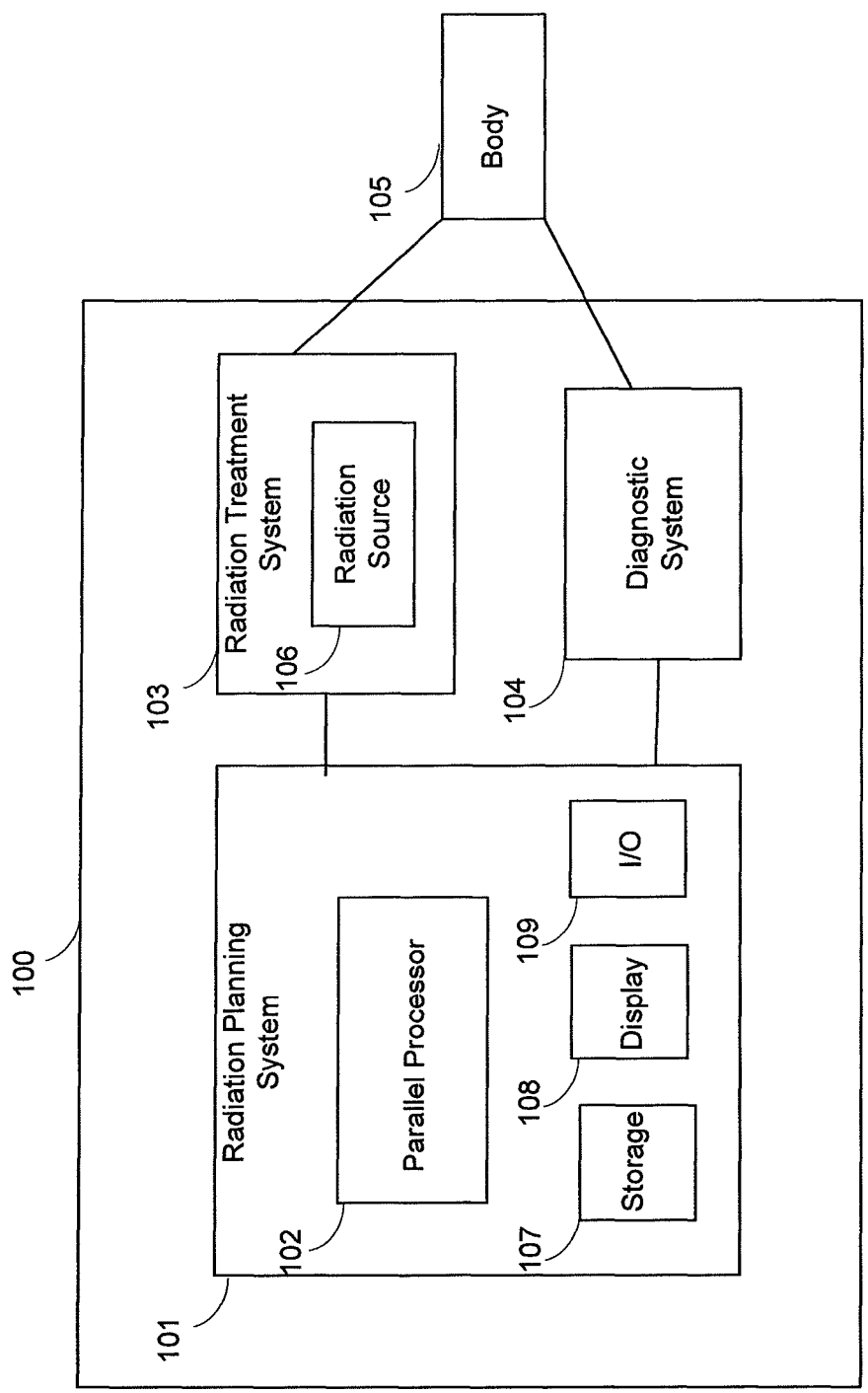
FIG. 1 shows a schematic diagram of an embodiment of the present invention.

FIG. 1 is a schematic diagram of a radiation therapy system 100 according to an embodiment of the current invention. Radiation therapy system 100 comprises a radiation planning system 101, which further comprises a parallel processor 102. Parallel processor 102 is adapted to receive input information concerning a body 105 having an intended radiation treatment region. Parallel processor 102 is also adapted to generate output information for providing radiation treatment to the intended radiation treatment region of the body 105. Parallel processor 102 is adapted to perform a plurality of reverse ray tracing calculations based on the received input information in determining the output information for providing radiation treatment. Each reverse ray tracing comprises calculating a first physical property corresponding to a first sub-region of the intended radiation treatment region of the body that is intersected by a ray traced from a source position through the intended radiation treatment region; and calculating, subsequent to the first-mentioned calculating, a second physical property corresponding to a second sub-region of the intended radiation treatment region that is intersected by the ray at a location closer to the source position than is the first sub-region. The radiation planning system 101 may further comprise storage 107, display 108, and I/O 109. Storage 107 may be, for example, a hard disk drive, a CD-ROM drive, a DVD drive, a flash drive, etc. Display 108 may be, for example, a Liquid Crystal Display (LCD), a cathode ray tube (CRT) monitor, a plasma display, etc. I/O device 109 may include, for example, a mouse, a keyboard, an interface for data transfer over a network or a data bus, etc.

Radiation therapy system 100 may further comprise a radiation treatment system 103 that is in communication with radiation planning system 101. Radiation treatment system 103 further comprises a radiation source 106. Radiation source 106 is a source that emits a beam of radiation to be directed onto body 105 for treatment. Examples of radiation sources may include, a X-ray source, a gamma ray source, an electron beam source, etc. Radiation source 106 may further comprise a multi-leaf collimator (MLC) to collimate the beam. By adjusting the position of the leaves of the MLC, a dosimetrist may match the radiation field to a shape of the treatment region of body 105. Other beam shaping and/or contouring can be included in some embodiments. Radiation source 106 can have a corresponding source model. Radiation system 103 may be controlled by radiation treatment planning system 101, for example, to deliver intensity modulated radiation energy to conform radiation treatment to the shape of the intended radiation treatment region of the body 105.

Radiation therapy system 100 may further comprise a diagnostic system, in communication with the radiation planning system 101, that generates empirical data of body 105. The empirical data may be used as input information to radiation planning system 101 and parallel processor 102 and may be used in reverse ray tracing calculations. Diagnostic system 104 comprises sensors to obtain the empirical data of body 105. An example diagnostic system may be a Computed Tomography (CT) scanner, a Magnetic Resonance Imaging (MRI) scanner, a Positron Emission Tomography (PET) scanner, etc.

Body 105 can be a human or an animal, for example.

The superposition/convolution algorithm has been shown to produce an accurate calculation of the dose distribution (Mackie, T. R., Scrimger, J. W., Battista, J. J., Med. Phys. 12, 188-196, 1985; Mackie, T. R., Ahnesjo, A., Dickof, P., Snider, A, Use of Comp. In Rad. Ther., 107-110 1987; Mackie, T. R., Reckwerdt, P. J., McNutt, T. R., Gehring, M., Sanders, C., Proceedings of the 1996 AAPM Summer School, 1996). It includes two stages. First, the incident fluence is transported through the density representation of the patient to compute the Total Energy Released per unit MAss (TERMA) at each location. The TERMA, $T_E(r')$, of a particular energy E of at point r' is defined as the fluence of energy E, $\Psi_E(r')$, weighted by the density relative to water, $\rho(r')$, and linear attenuation, $\mu_E(r')$, at point r', as shown in the following Eq 1.

$$T_E(r') = \frac{\mu_E(r')}{\rho(r')}\Psi_E(r'). \quad (1)$$

The linear attenuation coefficient, $\mu_E(r')$, is also dependent on the atomic material. Since Compton scattering dominates in the energy range of mega volts associated with radiation therapy and Compton scattering is dependent on electron density not material, clinically, there is a piecewise linear relation between standard CT numbers and density for normal human tissues. In general, non-Compton interactions are considered negligible in this energy range. The fluence, $\Psi_E(r')$, at point r' of energy E is determined by the source focal point s and the incident fluence $\Psi_{E,0}(r')$ of energy E in the direction r' according the following Eq. 2:

$$\Psi_E(r') = \frac{\Psi_{E,0}(r')}{\|r'-s\|^2}e^{\int_s^{r'}-\mu_E(t)dt}. \quad (2)$$

Then, the superposition/convolution algorithm spreads this energy by a dose deposition kernel to determine the final dose at each location. To allow the dose deposition kernel to scale realistically with tissue inhomogeneities the radiological distance between points, $d_p(r,r')$, is used, based on the following Eq. 3, which differentiates superposition from convolution.

$$d_\rho(r,r')=\int_r^{r'}\rho(t)dt. \quad (3)$$

The dose at point r, D(r), is computed from an integration over the TERMA volume weighted by the energy dependent dose deposition kernel, $K_E$, according to the following Eq. 4. The standard collapsed cone kernel is indexed by radiological distance and relative angle, $\omega$, between the point and the kernel axis, and lacks the geometric distance squared effect.

$$D(r) = \iiint \sum_E T_E(r')K_E(d_p(r,r'),\omega(r,r'))\frac{1}{\|r-r'\|^2}dr'. \quad (4)$$

Typically the mono-energetic contribution of every voxel, as in Eq. 4, is not calculated. Instead, as in Eq. 7, which is based on Eqs. 5 and 6, a discrete set of ray angles, $\omega$, and directions, $\nu$, are chosen and integrated along using a single poly-energetic kernel. This is justified by the approximately exponential kernel fall-off and the drastically reduced contribution of any single distant voxel due to the distance squared effect. The distance squared effect is negated by the increase in volume of the solid angle the rays represent. Ray directions are chosen to balance geometric and kernel energy factors.

$$T(r') = \sum_E T_E(r'). \quad (5)$$

$$K(d_r,\omega) = \sum_E K_E(d_r,\omega). \quad (6)$$

$$D(r) \approx \sum_{\omega,\nu} \int T(r+t\nu)K(d_p(r,r+t\nu),\omega)dt. \quad (7)$$

Traditionally, TERMA is calculated by casting a set of rays that deposit the incident fluence to volume according to Eqs. 1 and 2. For numerical accuracy, approximately four rays should pass through each TERMA voxel, attenuation should begin at the patient's surface and the fluence to each voxel should be normalized by the total length of the rays that contributed to that voxel. This normalization removes the normal inverse square fluence drop-off due to a diverging source. The normalization must therefore be reapplied, normally to the TERMA grid. A clinically acceptable speed enhancement is to not tilt the dose deposition kernel to align with the ray axis at each voxel. In this case it is more accurate to apply the divergence correction to the dose grid (Papanikolaou, N., Mackie, T. R., Meger-Wells, C., Gehring, M., Reckwerdt, P., Med. Phys. 20, 1327-1336, 1993).

TERMA is strongly dependent on the beam spectrum. The spectrum is rotationally symmetric about the beam axis and hardens with depth in material. By a hardened spectrum, we mean that the spectrum becomes more dominated by higher energy components as lower energy components are more preferentially scattered and absorbed out of the beam. Traditionally, the attenuation is modeled using a lookup table which when combined with the linear attenuation lookup table has axes of depth, density and off-axis angle. This table also requires the use of a fixed step ray-casting algorithm, which avoids evaluating the traditionally costly exponential at every step. Though clinically accepted for performance reasons, this look-up table assumes a homogenous medium. This is incorrect as heterogeneous tissues preferentially attenuate different spectra. Furthermore, the fixed step size and discretized rays results in numerical artifacts.

The dose deposition kernel also has a dependence on the energy spectrum at each voxel. However, this effect is negligible and a single poly-energetic kernel has been shown to be sufficiently accurate for clinical use and is the current standard of care. Poly-energetic kernels are created by combining a spectrum of mono-energetic kernels, which are generated using Monte Carlo simulations that forces mono-energetic photons to interact at the center of a water sphere and tallying the dose deposited everywhere in that sphere (Ahnesjo, A., Andreo, P., Brahme, A., Acta. Oncol., 26, 49-56, 1987; Mackie, T. R., Bielajew, A. F., Rogers, D. W. O., Battista, J. J., Phys. Med. Biol. 33, 1-20, 1988).

Algorithms for image processing have obviously been adapted to parallel or graphic processing unit (GPU) architectures. There are several ray cast, ray trace and volumetric visualization algorithms adapted in conventional graphics systems, for example. However, dose calculation for radiation therapy is fundamentally concerned with the interaction of a line with a volume while visualization algorithms are interested in a property of a line, such as its integral or maximum. This distinction renders many parallel ray tracing algorithms developed for visualization inapplicable for radiation therapy. Part of the traditional TERMA algorithm may be superficially similar to volumetric ray-casting although naïvely adapting the previous GPU implementation as done in (Krüger, J., Westermann, R., 2003) is impractical and would fail to produce accurate results. Because dose deposition deals primarily with electron interactions, it is fundamentally different from visualization algorithms.

According to an embodiment of the current invention, the superposition/convolution algorithm can be adapted to the GPU using a combination of NVIDA's Compute Unified Device Architecture (CUDA) software development environment and the Digital Mars' D programming language for our implementation. The following describes the details of the adaptation.

As discussed, superposition/convolution is a two stage algorithm: first the TERMA is calculated and then the dose deposition kernel is superimposed.

During the TERMA calculation, a standard forward TERMA algorithm may be implemented. This method requires overlapping scattered accumulation, which results in read-write conflicts when run in parallel. A read-write conflict occurs when threads simultaneously attempt to read, process and then write to the same memory, resulting in only the last update being recorded. This drastically reduces the effective number of contributing rays to each voxel to below the limit required for numerical accuracy. However, the divergent nature of the source may be utilized to create sets of rays guaranteed to be one voxel apart at all times. While individual sets are large enough to be efficiently run on the GPU, this serialization causes excessive GPU call overhead. The traditional 3D spectral attenuation lookup table exceeded the texture cache size, reducing performance. Performance can be improved by individually attenuating separate spectral bins, using shared memory to reduce register usage. This reduced the lookup to a small 2D texture of linear attenuation coefficients parameterized by energy and density. This may be enabled by the hardware accelerated exponential on the GPU. Accuracy can also be improved as the spectrum is correctly attenuated in heterogeneous media. However, the number of rays required for numerical accuracy exhibit an unclear relation with resolution, discretization effects can be evident, as will be discussed and computation may comprise a significant fraction of the total dose calculation time.

These issues can be avoided by an inverse TERMA algorithm according to some embodiments of the current invention. By rearranging equations (1), (2) and (5), separating the incidence fluence, $\Psi_{E,0}(r')$, into a spectral weight, $w_E$, and net fluence factor, $\Psi_0(r')$, and defining an attenuation factor, the following Eq. 8 is obtained.

$$A(r') = \frac{1}{\|r' - s\|^2} \sum_E w_E(r') \frac{\mu_E}{\rho(r')} e^{\int_s^{r'} -\mu_E(t) dt} \qquad (8)$$

Figure 2:
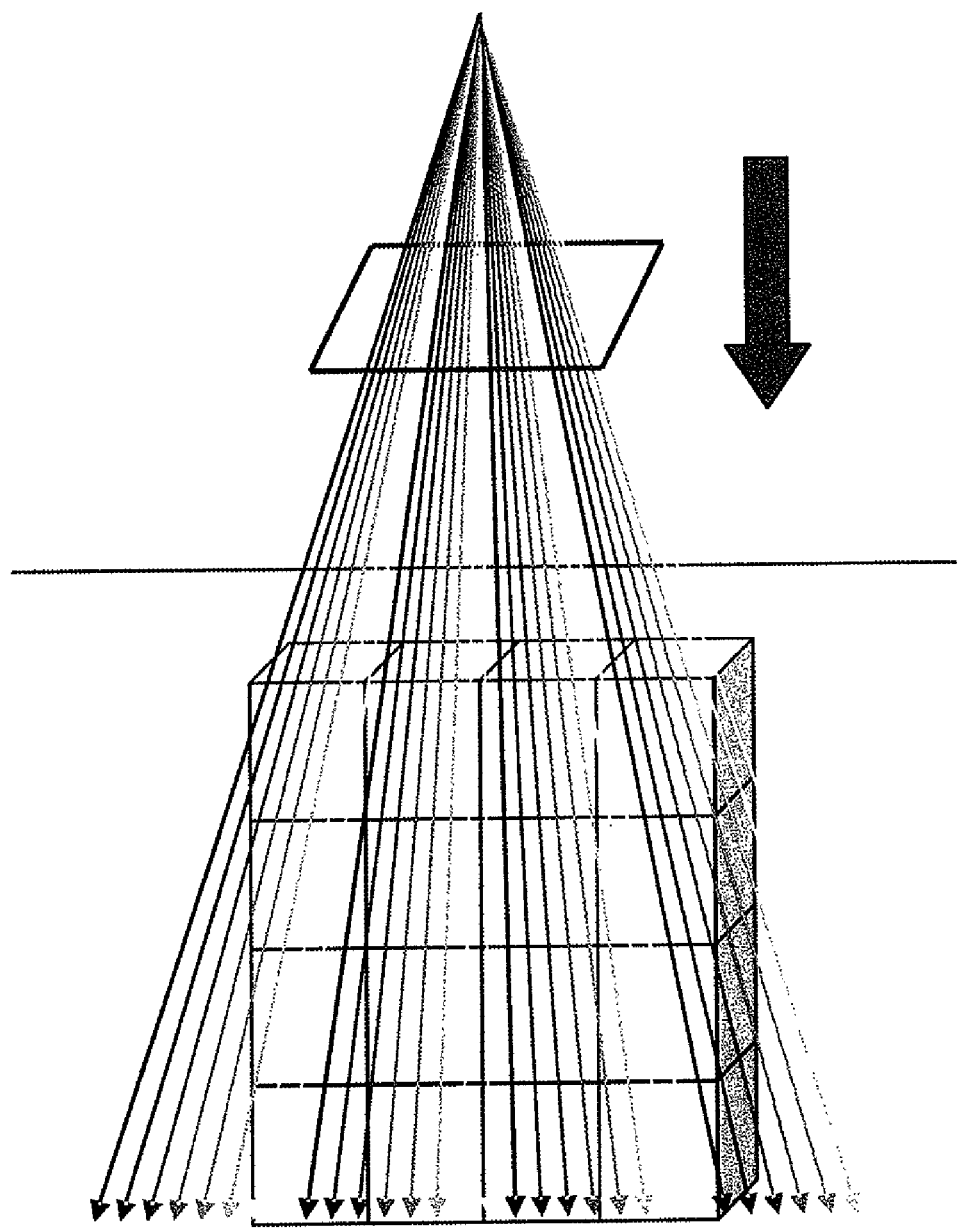
FIG. 2 illustrate a conventional forward ray tracing.
Figure 3:
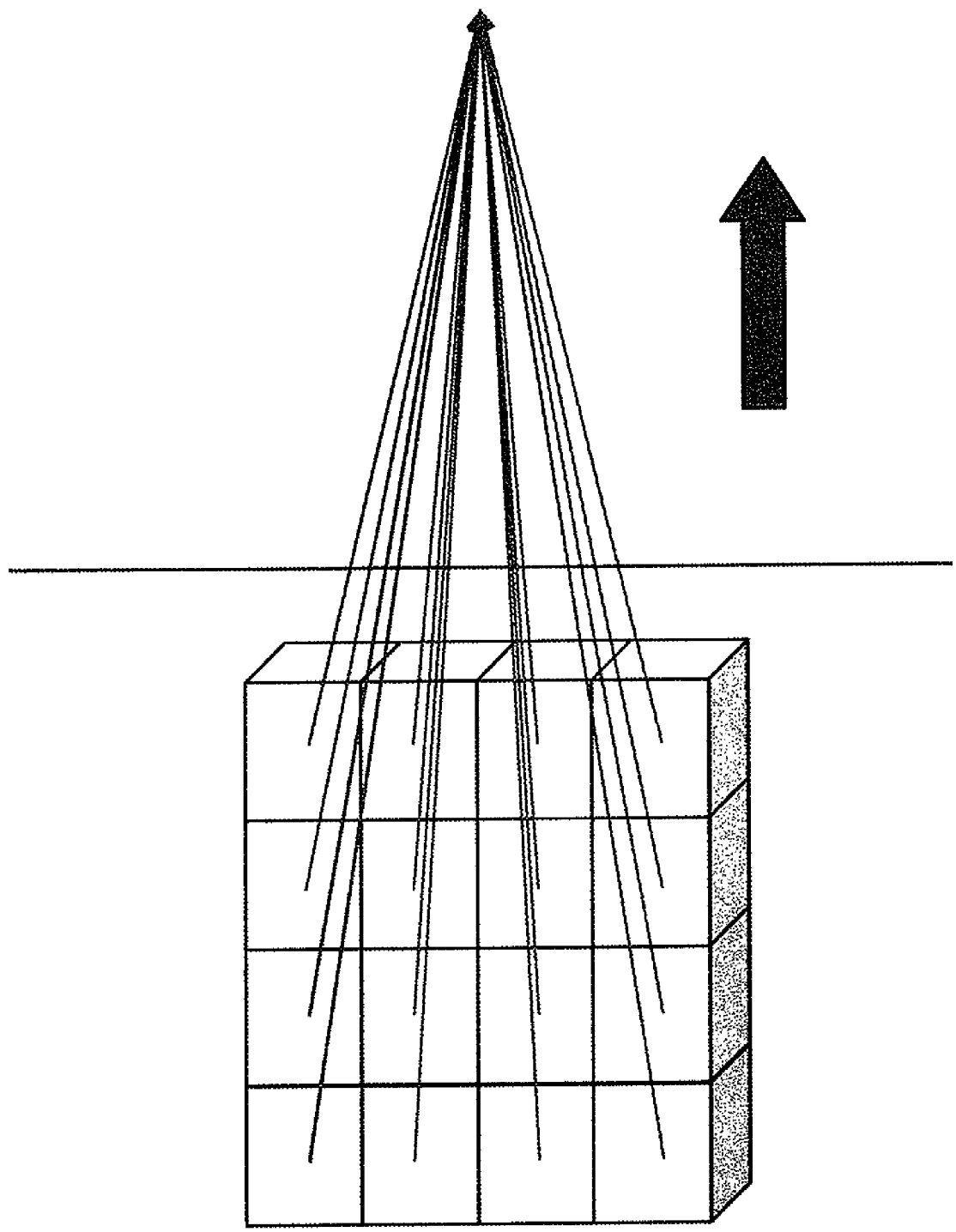
FIG. 3 illustrates a reverse ray tracing according to an embodiment of the present invention.

FIG. 2 illustrates a conventional forward ray tracing. FIG. 3 illustrates a reverse ray tracing according to an embodiment of the present invention. By casting a ray from each TERMA voxel back towards the source, gathering the net attenuation along the way, early ray termination can be achieved when the patient boundary is reached, increasing both performance and accuracy. In calculating the above defined attenuation factor, a pre-compiled look-up table may be used for the quantity $$\frac{\mu_E}{\rho}.$$

For example, based on a CT image, in Hounsfield units, of a radiation treatment region, one may look up this quantity from the look-up table. The spectral weight, $w_E$, for example, may be contained in a model of the radiation source for the radiation treatment, and each spectral bin may be attenuated independently for a given ray.

Then TERMA may then be calculated by multiplying the net attenuation for each voxel by the net incident fluence from the source towards that voxel according to the following Eq. 9:

$$T(r') = \Psi_0(r') A(r'). \qquad (9)$$

Figure 4:
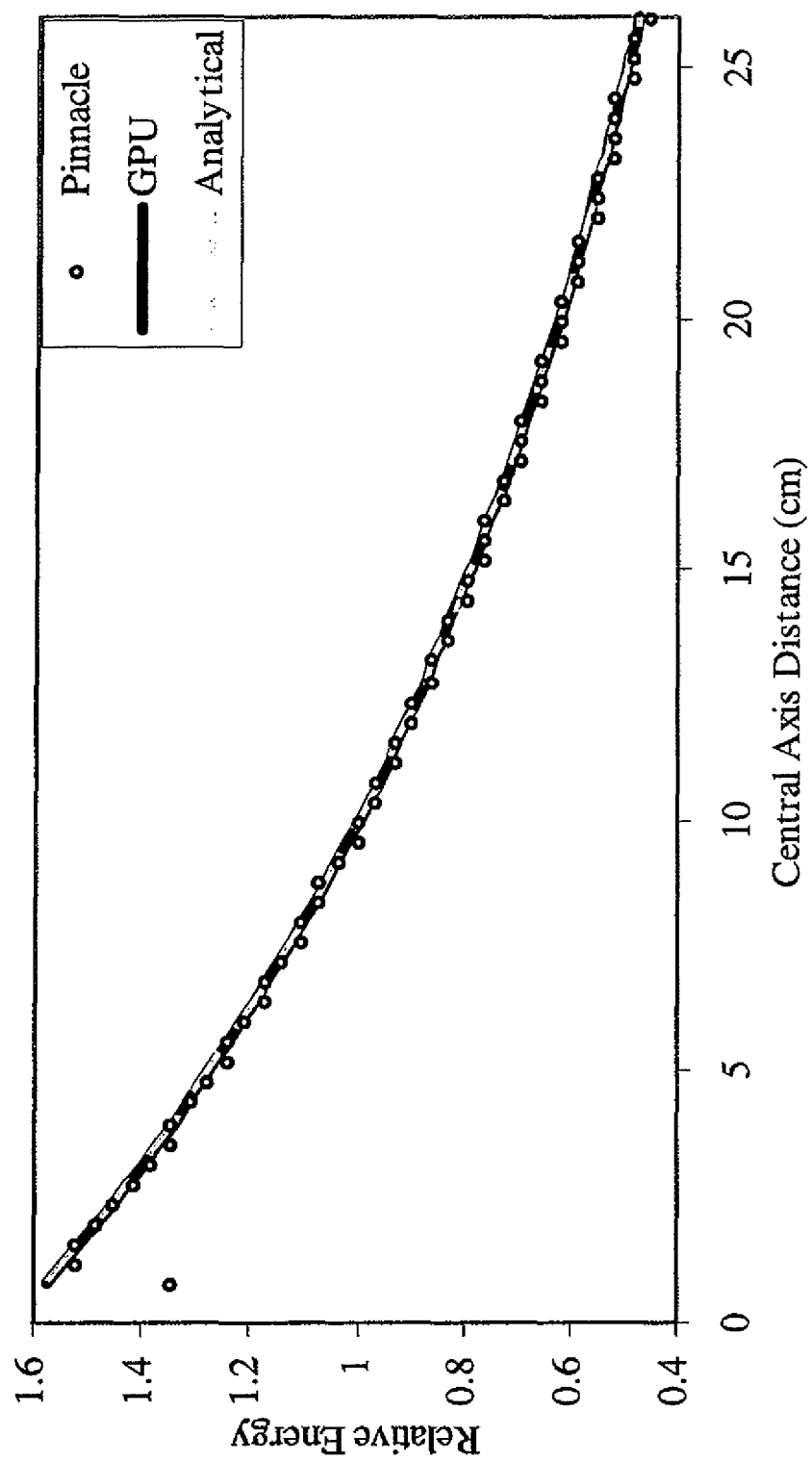
FIG. 4 shows the Total Energy Released per unit Mass (TERMA) along the central axis calculated analytically, using a commercial Pinnacle system (Philips Radiation Oncology Systems Madison Wis.) and an embodiment of the present invention, each normalized at a depth of 10 cm.

FIG. 4 shows TERMA energies along the central axis calculated analytically, using a commercial Pinnacle system (Philips Radiation Oncology Systems Madison Wis.), and according to an embodiment of the present invention, each normalized at a depth of 10 cm.

While Eq. 9 is an $O(n^4)$ algorithm, as opposed to the $O(n^3)$ for the standard forward method, each thread only writes to its own voxel, thus avoiding read-write conflicts. The algorithm allows for coalesced read access to texture memory which drastically enhances memory performance. Both the standard forward and the reverse ray-tracing algorithms may be used over a variety of clinical resolutions and may compute the computationally expensive attenuation volume once during interactive use or intensity modulation optimization, when only the fluence field is changed. This pre-computation can provide a multiple order of magnitude performance improvement according to some embodiments of the current invention.

TABLE 1

Performance of the standard forward, novel inverse and approximate TERMA calculation methods. Also included is the performance of only updating the incidence fluence field which is useful during intensity modulation.

| Size | Forward | Reverse | Approximate attenuation | Intensity Modulation |
|---|---|---|---|---|
| $32^3$ | 23 ms | 2 ms | 1 ms | 1 ms |
| $64^3$ | 44 ms | 18 ms | 2 ms | 1 ms |
| $128^3$ | 150 ms | 220 ms | 26 ms | 3 ms |
| $256^3$ | 1869 ms | 3317 ms | 454 ms | 13 ms |

Performance of the attenuation volume based TERMA algorithm relative to the traditional ray cast algorithm was compared across a variety of resolutions as shown in Table 1. Both methods incorporate physically correct multi-spectral attenuation and have been optimized for the GPU. Ray-cast, used in forward ray tracing calculations, can have read/write conflicts. The scalability of ray-cast exhibits sweet spots and required parameter tweaking to maintain the prerequisite number of rays traversing each voxel. The tweaking is laborious and highly unintuitive. The attenuation volume based TERMA computation by reverse ray tracing calculations exhibits an empirical performance of $O(n^{3.76})$, which is a slight improvement over its theoretical $O(n^4)$. Reverse ray tracing calculations, according to some embodiments of the current invention, does not suffer from read/write conflict. The fast, approximate radiological depth based attenuation algorithm, which makes the standard homogeneous material approximation, provided a speedup of ~8×. The performance of only updating the incident fluence, as commonly used in intensity modulation in treatment planning, is reported under intensity modulation.

Figure 5A:
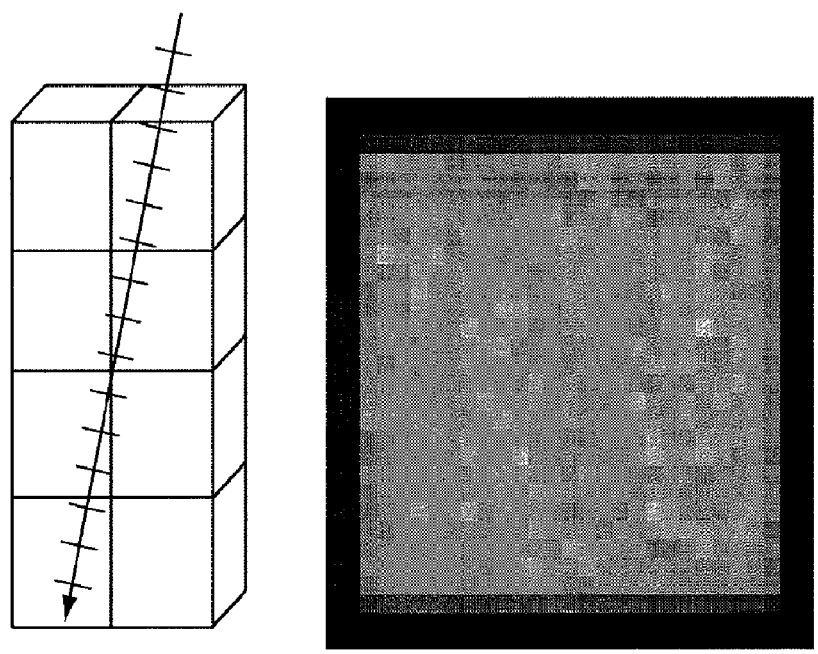
FIG. 5A shows a penumbra slice of TERMA with discretization artifacts calculated using forward tracing.
Figure 5B:
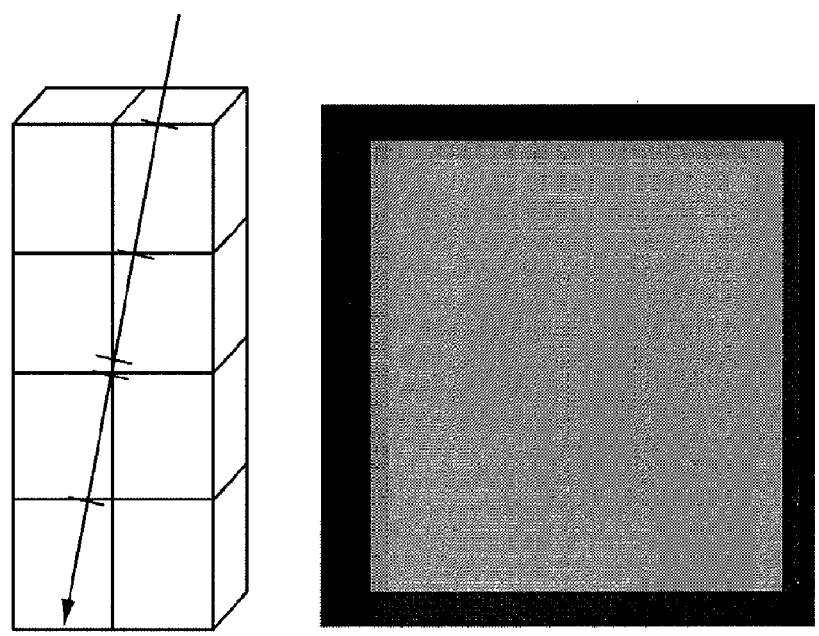
FIG. 5B shows the same penumbra slice of TERMA without discretization artifacts calculated using an embodiment of the present invention.

One advantage of the reverse ray tracing calculation is the elimination of artifacts due to ray discretization. This is because an exact radiological path can be used in the reverse ray-tracing method, similar to the rasterization method (Amanatides, J., Woo., A., Eurographics '87, Conference Proceedings, 1987), which reduces the per ray per voxel memory accesses to one and eliminates related discretization artifacts. FIGS. 5A and 5B show calculated slices of TERMA using a fixed step size and an exact radiological distance according to an embodiment of the present invention, respectively.

Figure 6A:
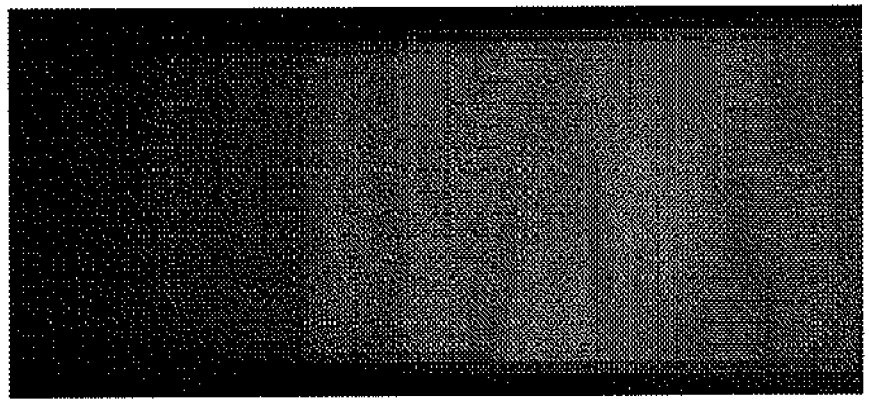
FIGS. 6A and 6B show calculated slices of TERMA using a fixed step size and an exact radiological distance according to an embodiment of the present invention, respectively.
Figure 6B:
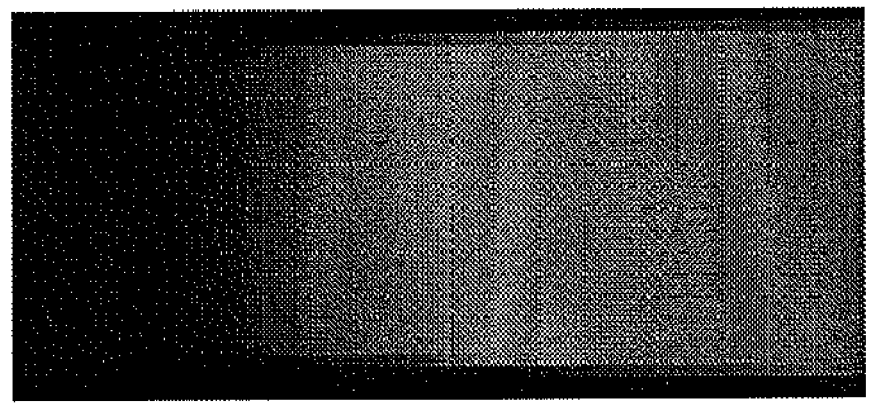

Further, physically correct multi-spectral attenuation (Liu, H. H., Mackie, T. R., McCullough, E. C., Med. Phys. 24, 1729-1741, 1997) can be applied in the reverse ray tracing calculations. For interactive beam angle changes, a simpler variant without physically correct multi-spectral attenuation can be implemented, as typically used in current clinical systems and can result in a significant performance improvement. During the TERMA calculation, physically correct multi-spectral attenuation (Liu, H. H., Mackie, T. R., McCullough, E. C., Med. Phys. 24, 1729-1741, 1997) can be used for the reverse ray calculations. The current clinical standard is a fixed-step, fast, approximate forward method which lacks physically correct multi-spectral attenuation. The use of a cached attenuation volume, as identified according to some embodiments of the current invention, can be used to accelerate the TERMA calculation. FIG. 6A shows a penumbra slice of TERMA with discretization artifacts calculated using the standard forward ray tracing without multi-spectral attenuation. FIG. 6B shows the same penumbra slice of TERMA without discretization artifacts calculated according to an embodiment of the present invention with multi-spectral attenuation.

Once TERMA is calculated, superposition of a dose deposition kernel to compute an amount of absorbed radiation energy can be applied. Superposition has two standard formulations. The forward formulation spreads dose from a TERMA voxel to the surrounding dose voxels. This forward formulation requires calculating the dose to every patient voxel and suffers from read-write conflicts as multiple TERMA voxels contribute to every dose voxel. The inverse kernel formulation gathers the contribution to a dose voxel from the surrounding TERMA voxels. This is computationally efficient as only the dose to the volume of interest is calculated. This is possible because the dose deposition kernel is invertible.

FIGS. 7A and 7B illustrate titled kernel and non-tilted kernel during the superposition operation. Strictly speaking, use of kernel tilting in standard superposition breaks the invertible kernel assumption. However, given the distant source and the kernel's rapid fall-off, invertibility is still a reasonable assumption and is in clinical use. Nonetheless, the kernel's rapid fall-off also creates numerical sampling issues at typical clinical resolutions. There are two standard alternatives. The cumulative kernel (CK) (Ahnesjo, A., Med. Phys. 16, 577-92, 1989) represents the dose deposition from a ray segment to a point, according to the following Eq. 10.

$$CK(x,\omega)=\int_0^x K(t,\omega)dt. \quad (10)$$

The cumulative-cumulative kernel (CCK) (Lu, W., Olivera, G. H., Chen, M., Reckwerdt, P. J., Mackie, T. R., Phys. Med. Biol. 50, 655-680, 2005) represents the dose deposition from a ray segment to a ray segment.

$$CCK(x,\omega)=\int_0^x CK(t,\omega)dt. \quad (11)$$

Both are derived from integrating the standard point to point kernel, $K(d_r, \omega)$, for particular radiological depths, $d_r$, and angles, $\omega$.

$$\int_x^{x+\Delta x} K(v,\omega)dv=CK(x+\Delta x,\omega)-CK(x,\omega). \quad (12)$$

$$\int_0^{\Delta s} CK(x+u,\omega)du=CCK(x+\Delta s,\omega)-CCK(x,\omega). \quad (13)$$

$$\int_0^{\Delta s}\int_{x+v}^{x+\Delta x+v} K(u,\omega)dudv=(CCK(x+\Delta s+\Delta x,\omega)-CCK(x+\Delta x,\omega))-(CCK(x+\Delta s,\omega)-CCK(x,\omega)). \quad (14)$$

While more accurate, particularly at coarser resolutions, the CCK formulation has traditionally been 50% slower than the CK formulation. However, the GPU's texture unit, which caches memory accesses and provides dedicated linear interpolation hardware, allows the use of the CCK formulation with a negligible performance decrease. Thus, the superposition calculation can be enhanced with the cumulative-cumulative kernel (Lu, W., Olivera, G. H., Chen, M., Reckwerdt, P. J., Mackie, T. R., Phys. Med. Biol. 50, 655-680, 2005).

Serial CPU implementations allows the reuse of ray-cast index calculation, by moving all indexes one voxel over. But, this prevents kernel tilting, resulting in errors at large off-axis angles, as will be discussed in Table 2. In contrast, some embodiments of the present invention implemented on a GPU allow both tilting and non-tilting kernels to be calculated. Kernel tilting has traditionally resulted in 300% loss in performance (Liu, H. H., Mackie, T. R., McCullough, E. C., Med. Phys. 24, 1729-1741, 1997), but some embodiments of the present invention implemented on a GPU has a performance loss of only 19%.

Because the superposition operation maintains accuracy at coarse resolutions and the kernel exhibits rapid fall-off at edges, a multi-resolution superposition algorithm that approximates each ray as a true solid angle can be employed according to some embodiments of the current invention. Unlike a ray, the width of a solid angle increases with geometric distance. In a discretized volume, a ray's width is proportional to the voxel's width. Therefore, by increasing the voxel width with geometric distance, a ray can approximate a solid angle. This approximation also increases the step size in a logarithmic manner which increases the performance by shrinking the computational complexity from $O(\omega DT^{1/3})$ to $O(\omega D \log(T^{1/3}))$; where $\omega$ is the number of angles, D is the number of dose voxels, and T is the number of TERMA voxels.

Compared to the standard method, the multi-resolution superposition according to an embodiment of the present invention exhibits an interesting accuracy trade-off. Table 2 compares the accuracy of the multi-resolution superposition algorithm according to some embodiments of the present invention to the standard methods across multiple field sizes and kernel ray samplings. The multi-resolution superposition algorithm according to some embodiments of the present invention generally can perform better in the penumbra and low dose regions for small field sizes, as less TERMA is geometrically missed by rays. However, accuracy in the high dose region may be compromised slightly as the larger steps can cause the beam boundary to be blurred. A variant of the multi-resolution superposition algorithm as a variant embodiment of the present invention, using the same step sizes, but not using a multi-resolution data structure can exhibit reduced cache performance and may increase the mean error by 60% on average.

liams, L., SIGGRAPH Comput. Graph. 17, 3, 1-11, 1983), as it is both efficient to calculate and has good cache performance. Resolution changes may be limited to a maximum of once per step and may be only allowed to occur at voxel boundaries in the coarser resolution. This can prevent a TERMA voxel from contributing multiple times to the same dose voxel. Kernel tilting may not be incorporated as adding tilting would increase the required registers beyond a performance threshold, dropping GPU occupancy from 25% to 17%.

Several strategies can be used to optimize Compute Unified Device Architecture (CUDA) performance. CUDA's execution model is a 2D grid of 3D blocks of threads which execute a function (called a kernel). Each block represents one parallel work unit and therefore is limited in size. Block thread counts were optimized using NVIDIA's CUDA occupancy calculator. For volume processing, a 1:1 mapping of threads to voxels in the x and y direction may be used. The z direction may be handled by looping over the per voxel function with increasing z indices. The stride may be the z block size, which maintains thread spatial cohesion. Increased thread spatial cohesion, enhanced by cube-like block dimensions, can reduce cache misses and improve performance. All input array data may be cached, generally in textures, which in the case of the superposition can provide a ~2x improvement in performance. Shared memory may be used to cache the array multi-resolution volume structures. Shared memory may also offer a performance improvement over registers for the multi-spectral TERMA calculation. A maximum number of 21 energy bins may be chosen as being both sufficient for high energy beams and free of bank conflicts.

TABLE 2

The average mean deposited dose error relative to $D_{max}$, the maximum deposited dose, for field sizes from 1 cm to 23 cm. Error is broken down by region with the penumbra region defined as having a dose gradient greater than 0.3 $D_{max}$ and the low dose region being below 0.2 $D_{max}$. Fields were square and size was defined at a depth of 10 cm Reference dose deposition was calculated using a tilted kernel sampled with 4608 rays. Pencil beam accuracy was approximated by truncating the superposition kernel at a 3 cm radius. An absolute dosimetry error of 2-5% is clinically acceptable (Ahnesjo, A., Aspradakis, M., Phys. Med. Biol. 44, R99-R155, 1999).

|  | High dose region | | | Penumbra region # of Rays | | | Low dose region | | |
| --- | --- | --- | --- | --- | --- | --- | --- | --- | --- |
|  | 80 | 72 | 32 | 80 | 72 | 32 | 80 | 72 | 32 |
| Tiled | 0.15% | 0.13% | 0.34% | 0.22% | 0.13% | 0.30% | 0.21% | 0.14% | 0.25% |
| Not-Tilted | 0.37% | 0.38% | 0.53% | 0.79% | 0.73% | 0.73% | 0.43% | 0.39% | 0.44% |
| Multi-Resolution | 0.64% | 0.55% | 0.76% | 0.76% | 0.78% | 0.81% | 0.37% | 0.39% | 0.38% |
| Pencil Beam | 5.92% | 5.98% | 5.83% | 2.77% | 2.81% | 2.69% | 1.68% | 1.69% | 1.68% |

Figure 8A:
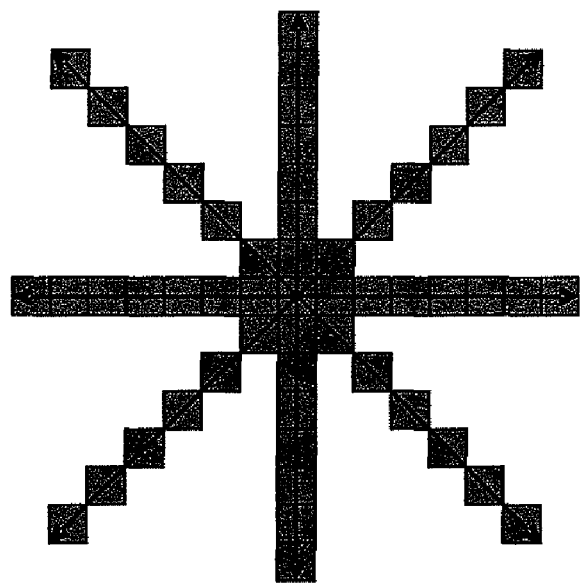
FIGS. 8A and 8B show the diagrams of the memory access patterns according to the conventional uniform sampling and a small field (5 mm) dose deposition slice calculated, respectively.
Figure 8B:
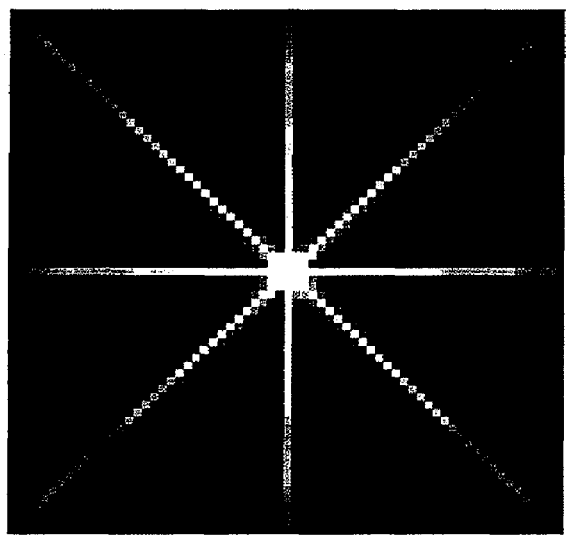
Figure 9A:
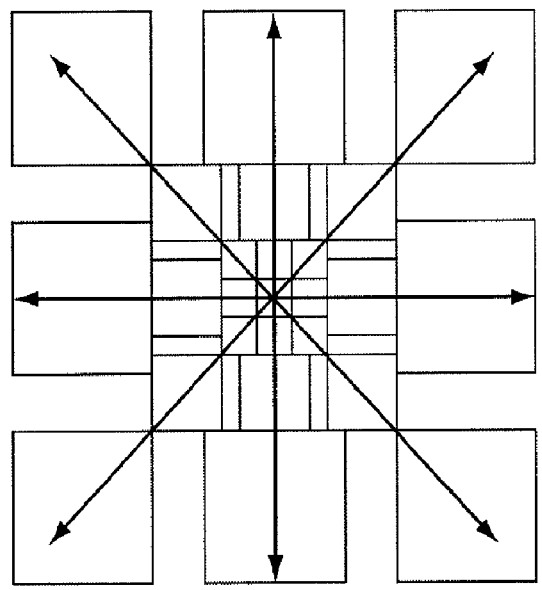
FIGS. 9A and 9B show the diagrams of the memory access patterns according to an embodiment of the present invention and a small field (5 mm) dose deposition slice calculated, respectively.
Figure 9B:
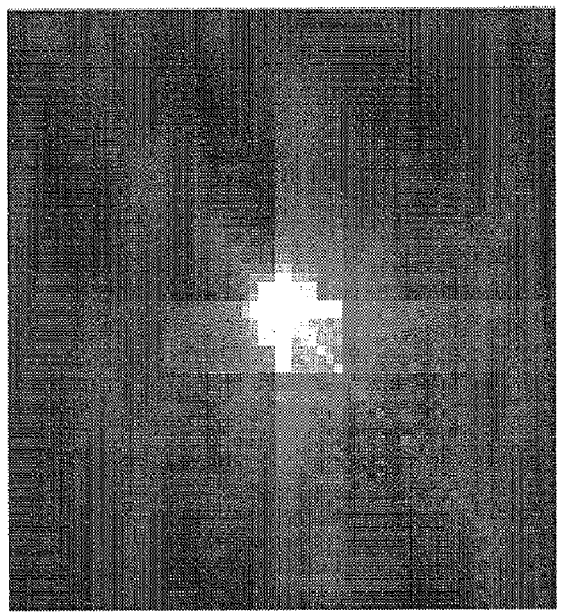

Small field artifacts, which occur when an entire beam is missed due to sparse ray sampling, can be reduced by using a multi-resolution grid according to some embodiments of the present invention. FIGS. 8A and 8B show the diagrams of the memory access patterns according to the conventional uniform sampling and a small field (5 mm) dose deposition slice calculated, respectively. FIGS. 9A and 9B show the diagrams of the memory access patterns according to an embodiment of the current invention using a multi-resolution grid and a small field (5 mm) dose deposition slice calculated, respectively.

However, larger step sizes can decrease the dose deposition kernel accuracy. Artifacts are introduced when neighbouring voxels transverse different coarse resolution voxels. It is noted that our implementation is inherently isotropic which tends to decrease the benefit of non-uniform angle sampling.

The multi-resolution algorithm can be implemented using a volumetric maximum intensity projection (MIP)-map (Wil- In both stages of TERMA computation and superposition according to an embodiment of the present invention, the standard fixed step size ray-cast algorithm may be replaced with an exact radiological path method, similar to line rasterization (Amanatides, J., Woo., A., Eurographics'87, Conference Proceedings, 1987).

Figure 10:
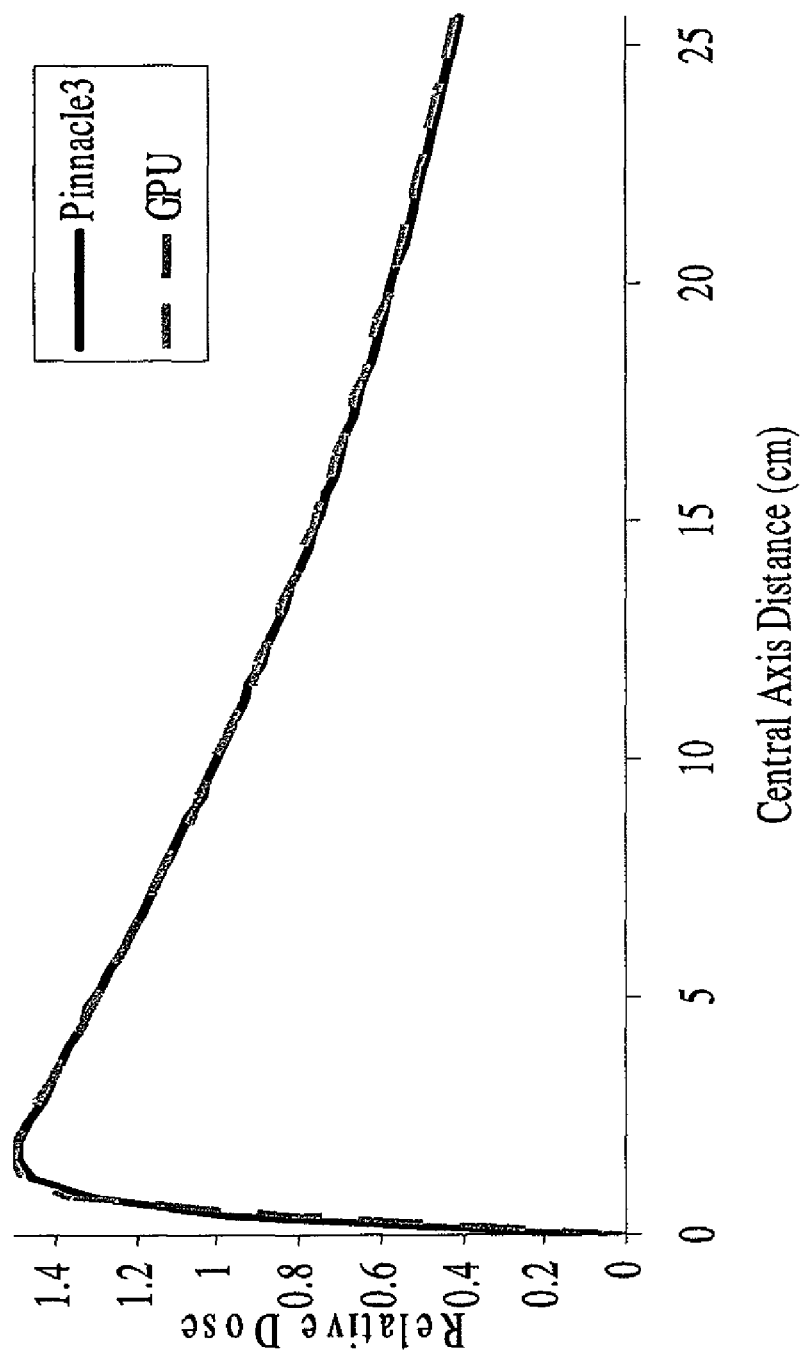
FIG. 10 shows absorbed dose patterns along the central axis calculated by a commercial Pinnacle system (Philips Radiation Oncology Systems Madison Wis.) and an embodiment of the present invention, each normalized at a depth of 10 cm.
Figure 11:
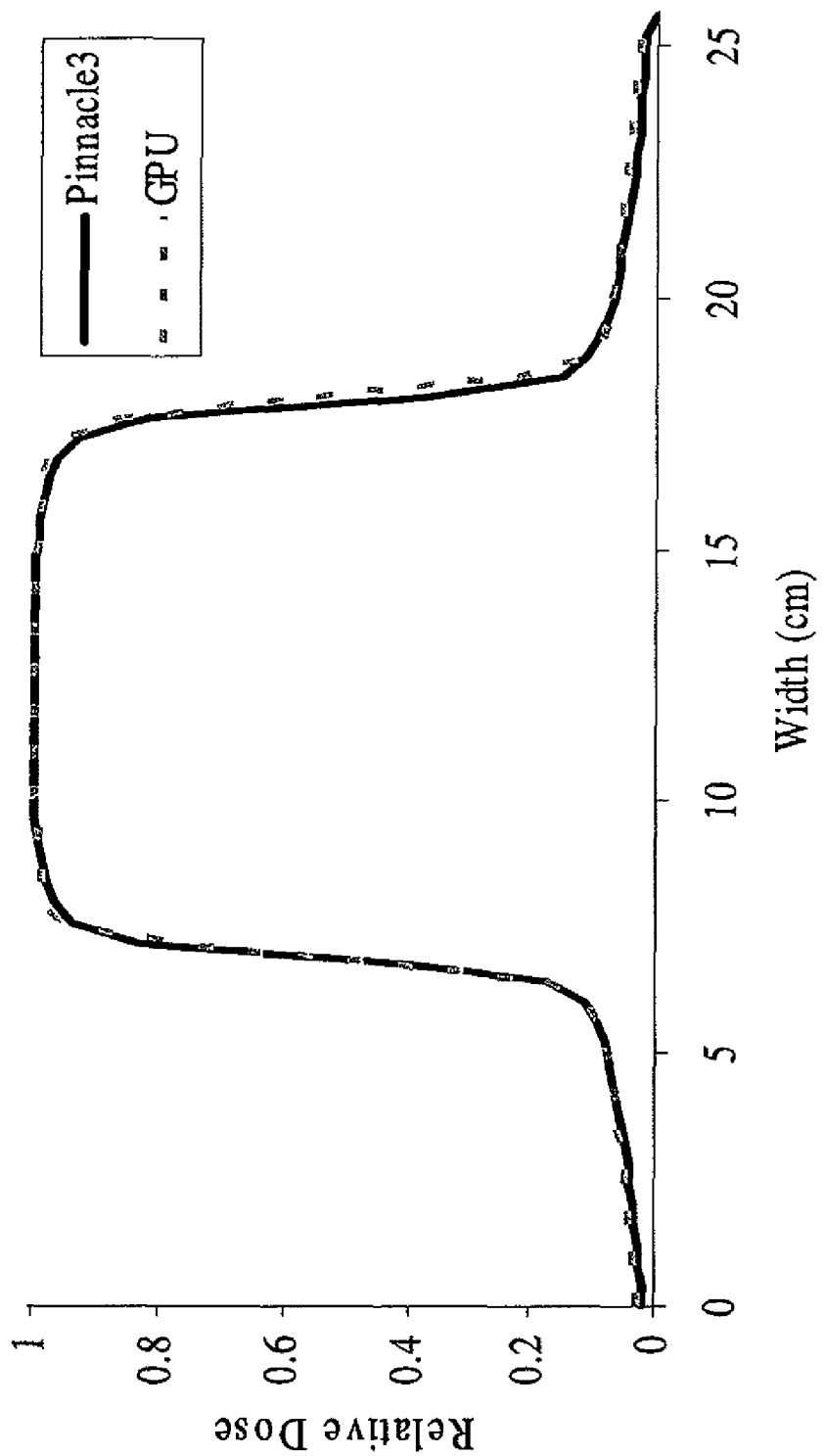
FIG. 11 shows absorbed dose profiles calculated by a commercial Pinnacle system (Philips Radiation Oncology Systems Madison Wis.) and an embodiment of the present invention at a depth of 10 cm, each normalized at the midpoint.

FIG. 10 shows absorbed dose patterns along the central axis calculated by a commercial Pinnacle system (Philips Radiation Oncology Systems Madison Wis.) and an embodiment of the present invention, each normalized at a depth of 10 cm. FIG. 11 shows absorbed dose profiles calculated by a commercial Pinnacle system and an embodiment of the present invention at a depth of 10 cm, each normalized at the midpoint.

Quantitative analysis of a transport algorithm, such as superposition/convolution, can be complicated by a strong dependence on the incidence fluence from the source model of the radiation source for the radiation treatment (Mohan, R., Chui, C., Lidofsky, L., Med. Phys. 12, 592-597, 1985; McNutt, T. R.: Dose Calculations, Philips white paper). The source model in turn needs to be optimized to minimize the error between measured dose and calculated dose. Thus, the source model often can mask errors in the transport algorithm. Furthermore, commercial systems may include a separate electron contamination model. In the preliminary experiments conducted using an embodiment of the current invention, only a simple source model is considered. The preliminary experiments yield results similar to those using the modeling parameters of a commercial treatment planning system, while providing an order of magnitude speed improvement as shown in Table 3.

TABLE 3

Comparison of dose engine performance on cube water phantoms. Rates reported in volumes per second (VPS). The tilting 32-ray kernel is more accurate than the non-tilting 80-ray kernel (See Table 2). Adaptive multi-grid methods (not implemented) have a speed-up factor of ~2x on clinical data.

| Engine | Kernel Type | Rays | $64^3$ Time (s) | VPS | Speedup | $128^3$ Time (s) | Speedup |
|---|---|---|---|---|---|---|---|
| GPU | CCK, Tilting | 72 | 0.198 | 5.051 | 41.8x | 2.801 | 33.7x |
| GPU | CCK, Non-tilting | 80 | 0.159 | 6.289 | 52.0x | 2.254 | 41.9x |
| GPU | CCK, Tilting | 32 | 0.086 | 11.628 | 96.1x | 1.246 | 75.8x |
| GPU | CCK, Multi-Resolution | 80 | 0.097 | 10.309 | 85.2x | 0.963 | 98.1x |
| GPU | CCK, Multi-Resolution | 32 | 0.042 | 23.810 | N/A | 0.411 | N/A |
| Pinnacle[3] | CK, Non-tilting | 80 | 8.268 | 0.121 | 1.0x | 94.508 | 1.0x |

In some experiments, clinical references were generated using the Pinnacle (Philips—Madison, Wis.) treatment planning system commissioned on clinical data from a Varian 6EX linear accelerator, providing a dose deposition, TERMA, transmission array, spectra, mass attenuation tables and mono-energetic dose deposition kernels. All experiments were run on an AMD Opteron 254 (2 cores, 2.8 GHz). Timing experiments were repeated at least ten times with no other programs active, using the standard superposition/convolution engine.

Timing results for an embodiment of the present invention were repeated multiple times using the high performance hardware counter of the CPU. Experiments were performed on a 3 GHz Pentium 4 with a single NVIDIA GeForce GTX 280. The 80-ray kernels used 10 zenith by 8 azimuth directions angles. The 32-ray kernels used 4 zenith by 8 azimuth directions. The tilting 72-ray kernel used 6 zenith by 12 azimuth directions, which provided higher accuracy (See Table 3). Total dose engine performance was determined from the sum of the source model, TERMA and superposition performance, excluding reusable calculations such as the flattening filter texture and the TERMA attenuation volume.

All tests were performed on a cube water phantom with a side length of 25.6 cm. Tests were performed on a volume with $64^3$ voxels, representative of standard clinical workload, and an additional high resolution volume with $128^3$ voxels. The multi-resolution superposition approach as an embodiment of the present invention, utilizes volumetric mip-maps and can performed 2-3 times faster than traditional superposition and performance scaled better to higher resolutions as shown.

Figure 12:
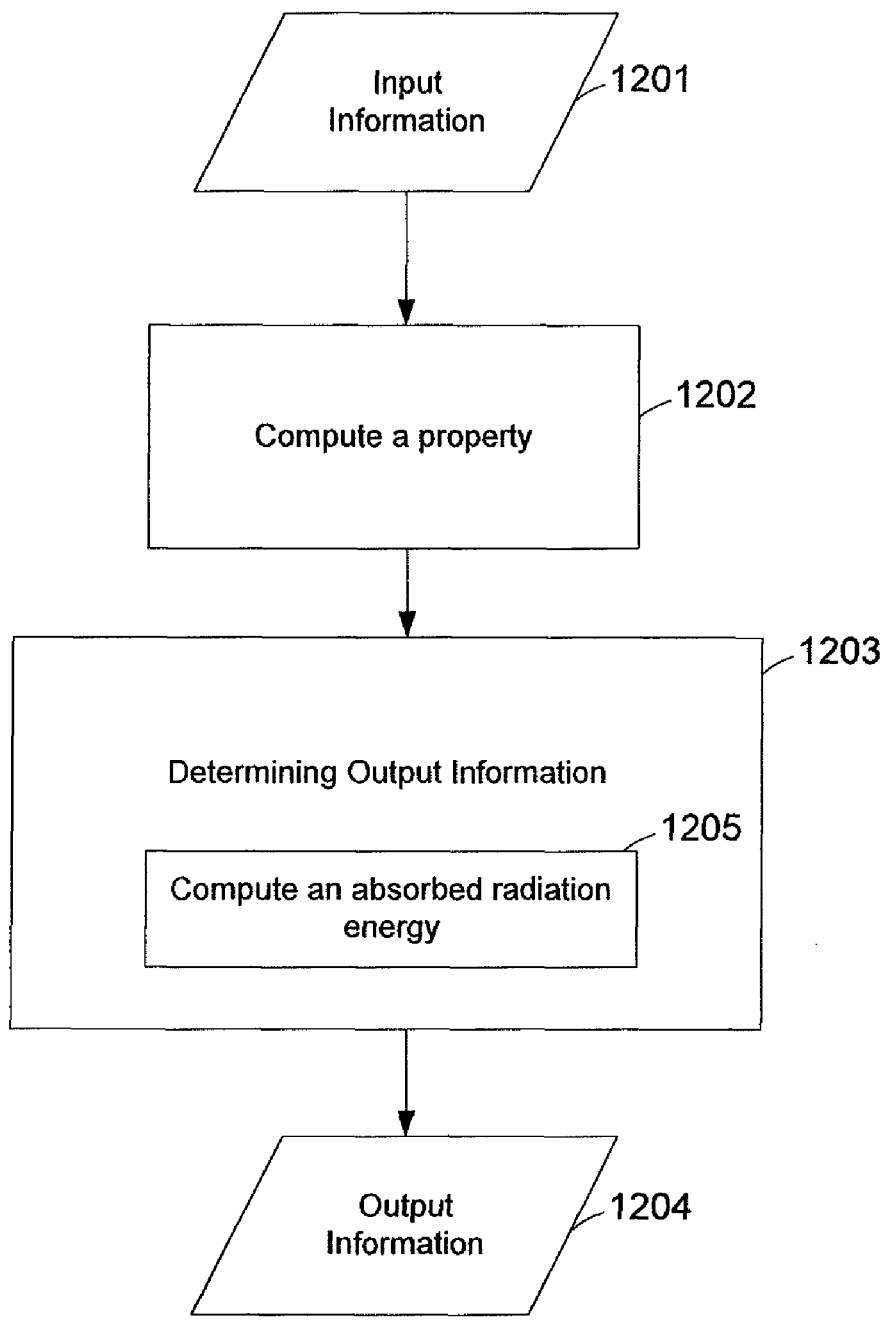
FIG. 12 illustrates a method according to another embodiment of the present invention.

FIG. 12 illustrates a method according to another embodiment of the present invention. The method comprises obtaining input information 1201 concerning a body having an intended radiation treatment region; in box 1202, computing based on input information 1201, in a direction from said body to a source position, a physical property at a first and second sub-regions along a ray traced from the source position through the body and intersecting the body in the intended radiation treatment region, the second sub-region along the ray being closer to the source position than the first sub-region along the ray; and in box 1203, determining output information 1204 for providing radiation treatment to the intended radiation treatment region.

In box 1202, the physical property at the second sub-region is computed based on the physical property computed at the first sub-region. The physical property is directed to an attenuation factor representing a relative amount of energy being extracted from an incident radiation beam. An example is the attenuation factor as discussed above. Further, the input information 1201 may comprise empirical data from the body. The measurement data may comprise at least one computed tomography (CT) image of the intended treatment region of the body. Additionally, at least one pre-compiled look-up table may be used in box 1202.

Box 1203 further comprises a step 1204 of computing an amount of radiation energy absorbed for the intended radiation treatment region. The absorbed radiation energy may be computed using at least one of a uniform sampling, a variable sampling, a multi-resolution grid, or variants thereof to cover the intended radiation treatment region. Further, the multi-resolution grid is assigned such that the ray traced from the source position through the body may approximate a solid angle.

Yet another embodiment of the invention may comprise a computer readable medium comprising software, which software when executed by a computer, causes the computer to implement the above method.

In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A system for radiation therapy comprising a radiation planning system,
   wherein said radiation planning system comprises a parallel processor adapted to receive input information concerning a body having an intended radiation treatment region and to output information for providing radiation treatment to said intended radiation treatment region of said body,
   wherein said parallel processor is adapted to perform a plurality of reverse ray tracing calculations based on said input information concerning said body in determining said output information for providing radiation treatment, each of said plurality of reverse ray tracing calculations comprising:
  calculating a first physical property corresponding to a first sub-region of said intended radiation treatment region of said body that is intersected by a ray traced between a source position and said intended radiation treatment region; and
  calculating, subsequent to the first-mentioned calculating, a second physical property corresponding to a second sub-region of said intended radiation treatment region that is intersected by said ray at a location closer to said source position than is said first sub-region.

2. The system of claim 1, wherein said calculating said physical property at said second sub-region depends on a result from said calculating said physical property at said first sub-region.

3. The system of claim 1, wherein said plurality of ray tracing calculations is at least two reverse ray tracing calculations performed substantially simultaneously by said parallel processor.

4. The system of claim 1, wherein said first and second physical properties correspond to an attenuation factor representing a relative amount of energy extracted from an incident beam of radiation.

5. The system of claim 1, wherein said input information concerning said body having said intended radiation treatment region comprises empirical data from said body.

6. The system of claim 5, wherein said empirical data comprises computed tomography (CT) image data of said intended radiation treatment region.

7. The system of claim 1, wherein said input information concerning said body having said intended radiation treatment region comprises a pre-compiled look-up table.

8. The system of claim 1, wherein said parallel processor is further adapted to compute an amount of radiation energy that would be absorbed by said intended region of radiation treatment based on said input information.

9. The system of claim 1, wherein said first and second sub-regions are substantially equal in size and shape corresponding to substantially equal number of voxels.

10. The system of claim 1, wherein said first sub-region is larger than said second sub-region.

11. The system of claim 1, further comprising a radiation treatment system, in communication with said radiation planning system, said radiation treatment system comprising a radiation source.

12. The system of claim 1, wherein said radiation source is adapted for intensity modulated radiation therapy to conform said radiation treatment to a shape of said intended radiation treatment region of said body.

13. The system of claim 1, wherein said radiation source is a source of high energy photons having an average photon energy of at least 1 MeV.

14. The system as in claim 1, further comprising a diagnostic system, in communication with said radiation planning system, said diagnostic system comprising sensors to obtain empirical data from said body to be input into said radiation planning system.

15. The system as in claim 14, wherein said diagnostic system is a CT scanner.

16. The system as in claim 1, wherein said parallel processor is a general purpose graphic processing unit.

17. The system as in claim 1, wherein said body is at least one of a human or an animal.

18. A method of determining radiation therapy parameters, comprising:
  obtaining information concerning an intended radiation treatment region of a body;
  computing, based on said information, in a direction from said body to a source position, a physical property at a first sub-region and a second sub-region along a ray that is traced between said source position and said body and intersecting said body in said intended radiation treatment region, said second sub-region along said ray being closer to said source position than said first sub-region along said ray; and
  determining said radiation therapy parameters for providing radiation treatment to said intended radiation treatment region based on said computing.

19. The method of claim 18, wherein said determining said radiation therapy parameters further comprises computing an amount of radiation energy that would be absorbed for said intended radiation treatment region.

20. The method of claim 19, wherein said first and second sub-regions are substantially equal in size and shape corresponding to substantially equal number of voxels.

21. A non-transient computer readable medium, containing software, which software when executed by a computer, causes the computer to implement the method of claim 20.

22. A non-transient computer readable medium, containing software, which software when executed by a computer, causes the computer to implement the method of claim 19.

23. The method of claim 20, wherein said first sub-region is larger than said second sub-region.

24. A non-transient computer readable medium, containing software, which software when executed by a computer, causes the computer to implement the method of claim 23.

25. The method of claim 18, wherein said physical property at said second sub-region is computed based on said physical property computed at said first sub-region.

26. A non-transient computer readable medium, containing software, which software when executed by a computer, causes the computer to implement the method of claim 25.

27. The method of claim 18, wherein said physical property is an attenuation factor representing a relative amount of energy extracted from an incident beam of radiation.

28. A non-transient computer readable medium, containing software, which software when executed by a computer, causes the computer to implement the method of claim 27.

29. The method of claim 18, wherein said information comprises empirical data from said body having said intended radiation treatment region.

30. The system as in claim 29, wherein said empirical data comprises a computed tomography (CT) image data of said intended radiation treatment region.

31. A non-transient computer readable medium, containing software, which software when executed by a computer, causes the computer to implement the method of claim 29.

32. A non-transient computer readable medium, containing software, which software when executed by a computer, causes the computer to implement the method of claim 30.

33. The system as in claim 18, wherein said information comprises a pre-compiled look-up table.

34. A non-transient computer readable medium, containing software, which software when executed by a computer, causes the computer to implement the method of claim 33.

35. A non-transient computer readable medium, containing software, which software when executed by a computer, causes the computer to implement the method of claim 18.

* * * * *